United States Patent
Cooney (10) Patent No.: US 10,966,855 B2
(45) Date of Patent: Apr. 6, 2021

(54) ORTHOSIS

(71) Applicant: Orthotic Composites Limited, London (GB)

(72) Inventor: Timothy Cooney, London (GB)

(73) Assignee: THUASNE UK LIMITED, Tunbridge Wells (GB)

( * ) Notice: Subject to any disclaimer, the term of this patent is extended or adjusted under 35 U.S.C. 154(b) by 743 days.

(21) Appl. No.: 15/615,419

(22) Filed: Jun. 6, 2017

(65) Prior Publication Data

US 2017/0348132 A1  Dec. 7, 2017

Related U.S. Application Data

(60) Provisional application No. 62/352,030, filed on Jun. 20, 2016.

(30) Foreign Application Priority Data

Jun. 7, 2016 (GB) .................................. 1609908

(51) Int. Cl.
*A61F 5/01* (2006.01)

(52) U.S. Cl.
CPC .............. *A61F 5/0127* (2013.01); *A61F 5/01* (2013.01); *A61F 5/0102* (2013.01); *A61F 5/0111* (2013.01); *B32B 2255/02* (2013.01); *B32B 2260/046* (2013.01)

(58) Field of Classification Search
CPC ........ A61F 5/01; A61F 5/0102; A61F 5/0104; A61F 5/0111; A61F 5/0113; A61F 5/0127; A61F 13/06; A61F 2/6607; A61F 2007/0045; A61F 2/30; A61F 5/0195; A61F 5/0585; A61F 13/067; A61F 13/064; B32B 2260/046; B32B 2255/02

USPC ...................................................... 602/23, 28
See application file for complete search history.

(56) References Cited

U.S. PATENT DOCUMENTS

| | | | | |
|---|---|---|---|---|
| 4,738,262 A | * | 4/1988 | Zebrack | A43B 7/00 36/116 |
| 5,230,170 A | * | 7/1993 | Dahle | A43B 7/02 36/2.6 |
| 5,624,386 A | * | 4/1997 | Tailor | A61F 5/01 428/110 |
| 5,897,515 A | * | 4/1999 | Willner | A61F 5/0111 602/27 |

(Continued)

FOREIGN PATENT DOCUMENTS

| | | | | |
|---|---|---|---|---|
| WO | 2001034071 A1 | | 5/2001 | |
| WO | WO-0134071 A1 | * | 5/2001 | ............ A61F 5/0111 |
| WO | 2004043289 A2 | | 5/2004 | |

OTHER PUBLICATIONS

Search Report dated Dec. 6, 2016 for GB priority document, GB 1609908.7.

(Continued)

*Primary Examiner* — Ophelia A Hawthorne
(74) *Attorney, Agent, or Firm* — Fisherbroyles, LLP; Victoria L. Boyd (57) ABSTRACT

An orthosis comprises a first portion which comprises a polymer reinforced with a plurality of first fibres, and a second portion which is disposed around at least a section of a peripheral edge of the orthosis which comprises a polymer reinforced with a plurality of second fibres. The first portion has a higher tensile strength and is harder than the second portion.

19 Claims, 8 Drawing Sheets

(56) References Cited

U.S. PATENT DOCUMENTS

| | | | |
|---|---|---|---|
| 6,044,577 A * | 4/2000 | Clark | A43B 7/081 36/29 |
| 2004/0102727 A1 | 5/2004 | Smits | |
| 2005/0054959 A1* | 3/2005 | Ingimundarson | A43B 13/026 602/5 |
| 2005/0054963 A1 | 3/2005 | Ingimundarson | |
| 2014/0358057 A1* | 12/2014 | Bradshaw | A61F 5/0111 602/28 |
| 2015/0105708 A1* | 4/2015 | Young | A61F 5/0102 602/5 |

OTHER PUBLICATIONS

International Search Report and Written Opinion for PCT/GB2017/051628 dated Sep. 4, 2017.

* cited by examiner

ORTHOSIS

The present invention relates to orthotic devices. More specifically, the present invention relates to an orthosis per se, and to a method of making the orthosis.

The use of high strength and lightweight materials in the manufacture of orthotics can have clinical advantages. For instance, in studies of the lower limb, it has been demonstrated that lower weight ankle foot orthotics (AFOs) decrease energy expenditure in walking and can increase cadence in a patient. An AFO consists of a lower footplate, which supports the patient's foot, an elongate strut extending up and around the patient's ankle, and a cuff by which the AFO is secured to the patient's calf. It has been found that composite fibre materials can be effectively employed to offer an orthotic force pattern, i.e. the application of a force on pressure tolerant areas of a person's anatomy using an orthosis to force a biomechanical change, whilst simultaneously being lightweight and strong.

When 'fitting' a pre-fabricated AFO to a patient, a specialist medical practitioner or orthotist usually needs to trim areas of the AFO, especially around the peripheral edge of the footplate, as one size of pre-fabricated AFO will be required to fit a range of different foot/shoe sizes. However, trimming composite fibre materials is difficult. For some orthotists who are mobile between hospital or business locations it is likely that the only tooling available to them would be household scissors, which would not be capable of trimming many types of orthotic composites. For this reason, an orthotist that does not have access to suitable trimming tooling/machinery may need to use AFOs comprising plastics, such as polypropylene or polypropylene, instead of composite fibres. These AFOs can be easily trimmed using scissors, thereby allowing the practitioner to fit the AFO for a given user. However, a plastic AFO may not be as lightweight and/or as strong as a composite fibre AFO, and so may provide the user with an inferior medical outcome compared to that when a composite fibre AFO is used.

The present invention arises from the inventor's work in trying to overcome the problems associated with the prior art.

In accordance with a first aspect of the invention, there is provided an orthosis comprising a first portion which comprises a polymer reinforced with a plurality of first fibres, and a second portion which is disposed around at least a section of a peripheral edge of the orthosis and comprises a polymer reinforced with a plurality of second fibres, wherein the first portion has a higher tensile strength and is harder than the second portion.

Advantageously, the second portion is easier to cut than the first portion, due to it being less hard. Accordingly, the second portion can be readily trimmed, for example with scissors as opposed to specialist tools, to better fit the orthosis to a subject.

Furthermore, the subject can even fit the orthosis to themselves, and cut it to shape without the need for assistance from an orthotist. Additionally, since the first portion has a higher tensile strength than the second portion, the orthosis is stronger than it would be if the polymer was only reinforced with the plurality of second fibres, and so provides a superior medical outcome compared to that when a plastic orthosis is used.

Preferably, the first fibres comprise carbon fibres. More preferably, the first fibres consist of carbon fibres. Accordingly, the only fibres in the first portion are preferably carbon fibres.

Advantageously, due to the carbon fibre reinforced polymer, the first portion is very strong and lightweight.

The first fibres may comprise unwoven fibres. The unwoven fibres may comprise unidirectional fibres.

Additionally, or alternatively, the first fibres may comprise woven fibres. The woven fibres may comprise twill fibres.

In a preferred embodiment, the first fibres comprise both unwoven and woven fibres. In a more preferred embodiment, the first fibres comprise both unidirectional fibres and twill fibres. In an even more preferred embodiment, the first fibres comprise both unidirectional carbon fibres and twill carbon fibres. In a most preferred embodiment, the first fibres comprise unidirectional carbon fibres sandwiched between twill carbon fibres.

Advantageously, the unidirectional fibres strengthen the orthosis along the axis to which they are aligned. Additionally, the twill fibres provide the orthosis with transverse strength.

Preferably, the second fibres comprise glass fibres. More preferably, the second fibres consist of glass fibres. Accordingly, the only fibres in the second portion are preferably glass fibres.

Advantageously, the second portion can be easily cut with scissors, allowing the orthosis to be adjusted for an individual subject.

The second fibres may comprise unwoven fibres. The unwoven fibres may comprise unidirectional fibres. Additionally, or alternatively, the second fibres may comprise woven fibres. The woven fibres may comprise twill fibres.

In a preferred embodiment the second fibres comprise twill glass fibres.

Preferably, the orthosis comprises a third portion disposed between the first and second portions, and comprising a polymer reinforced with a plurality of first and second fibres.

Advantageously, the third portion provides a join between the first and second portions.

In a preferred embodiment, the third portion comprises a plurality of first fibres sandwiched between a plurality of second fibres. In a most preferred embodiment, the third portion comprises the plurality of first fibres sandwiched between the plurality of second fibres, wherein the plurality of first fibres comprises unidirectional carbon fibres sandwiched between twill carbon fibres, and the plurality of second fibres comprises twill glass fibres.

Preferably, the polymer comprises a thermoplastic material or a thermosetting material.

In one preferred embodiment, the polymer comprises a thermoplastic material. The thermoplastic material is preferably selected from the group consisting of: polyethylene; polypropylene; modified polyethylene terephthalate; polyamide; polyethylene terephthalate; polyether imide; polyether sulfone; and polyether ketone.

However, in a more preferred embodiment, the polymer comprises a thermosetting material. The thermosetting material is preferably selected from the group consisting of: epoxy thermosetting resin; phenolic thermosetting resin; polyester thermosetting resin; polyurethane thermosetting resin; and silicon thermosetting resin. The thermosetting material is most preferably an epoxy thermosetting material.

Preferably, the first portion is substantially opaque. In embodiments where the first fibres comprise carbon fibres, it will be appreciated that the first portion will be a predominantly black in colour.

Preferably, the second portion is substantially translucent or transparent. Advantageously, the second portion (which is trimmable) can therefore be easily identified by the orthotist or subject without the need for additional labels to be printed thereon, which may require the use of heat and/or water etc.

Preferably, the second portion comprises a pigment and/or a dye which affects the colour of the second portion. The pigment may be a polyester and/or epoxy pigment disposed in the polymer. Preferably, the pigment and/or dye is selected to ensure that the second portion is visually distinct from the first portion. The third portion may also comprise the dye and/or pigment.

The amount of pigment and/or dye in the polymer in the second portion may be between 0.01 wt % and 20 wt %. Preferably, the amount of pigment and/or dye in the polymer in the second portion is between 0.05 wt % and 10 wt %. More preferably, the amount of pigment and/or dye in the polymer in the second portion is between 0.1 wt % and 5 wt %, between 0.02 wt % and 4 wt %, between 0.03 wt % and 3 wt %, or between 0.04 wt % and 2 wt %. Most preferably, the amount of pigment and/or dye in the polymer in the second portion is between 0.5 wt % and 1.5 wt %.

Accordingly, the second (and in some embodiments third) portion may be any colour which is distinct from the black carbon fibres of the first portion, such as red, orange, yellow, green, blue or purple. The inventors have successfully produced an orthotic device using a royal blue epoxy pigment.

The orthosis may comprise an upper-limb orthosis, a lower-limb orthosis or a spinal orthosis. The upper limb orthosis may be selected from the group consisting of a clavicular and shoulder orthosis, an arm orthosis, an elbow orthosis, a forearm-wrist orthosis, a forearm-wrist-thumb orthosis, a forearm-wrist-hand orthosis, a hand orthosis, and an upper-extremity orthosis. The lower limb orthosis may be selected from the group consisting of a foot orthosis, an ankle-foot orthosis (AFO), a knee-ankle-foot orthosis (KAFO), a knee orthosis and a hip-knee-ankle-foot orthosis (HKAFO).

In a preferred embodiment, the orthosis comprises a foot orthosis, an ankle-foot orthosis (AFO), a knee-ankle-foot orthosis (KAFO) or a hip-knee-ankle-foot orthosis (HKAFO). Most preferably, the orthosis is an ankle-foot orthosis (AFO).

Preferably, the orthosis comprises a footplate configured to extend beneath the sole of a foot of a subject. Preferably, the footplate comprises a front which extends beneath the toes of the subject, a back which extends beneath the heel of the subject, and two sides which extend between the front and the back.

Preferably, the orthosis comprises a calf abutment member for abutting the calf of a subject. Preferably, the orthosis comprises a strut extending between the footplate and the calf abutment member. Preferably, the strut is connected to the footplate at a location which is configured to be posterior (i.e. behind) to the ankle axis of a subject wearing the orthosis.

Advantageously, the strut is under more tensile loading than compressive loading. Accordingly, due to the high tensile strength of the first portion a strut configured to be posterior to the ankle axis needs less material than a strut anterior (i.e. in front) to the ankle axis which would be subjected to more compressive loading.

Preferably, the strut is configured to extend over the back of a leg of the subject. Preferably, the strut is not configured to extend over the front of the leg of the subject.

Preferably, the orthosis comprises a releasable fastener for fastening the calf abutment member to a leg of the subject. The releasable fastener may comprise a strap for connecting opposite ends of the calf abutment member. Thus, the calf abutment member and the strap may be configured to encircle the calf of the subject, and tightening the strap may fasten the orthosis. The strap may be held in position by means of a Velcro fastener.

Preferably, the area at least adjacent and/or towards the front of the footplate comprises the second portion. Accordingly, the second portion preferably defines an extension to the length of the footplate.

The extension to the length of the footplate preferably increases the length of the footplate by at least 0.5 cm at its longest point, more preferably by at least 1.0 cm or 1.5 cm at its longest point, and most preferably by at least 2.0 cm or 2.5 cm at its longest point.

The extension to the length of the footplate preferably increases the length of the footplate by between 0.5 cm and 10.0 cm at its longest point, more preferably by between 1.0 cm and 7.5 cm or between 1.5 cm and 5.0 cm at its longest point, and most preferably by between 2.0 cm and 4.0 cm or between 2.5 cm and 3.5 cm at its longest point.

Alternatively, or additionally, the area at least adjacent and/or towards a region of one or both sides of the footplate comprises the second portion. Preferably, the area at least adjacent and/or towards a region of one or both sides of the footplate is also at least adjacent and/or towards the front of the footplate. Accordingly, the second portion preferably defines an extension to the width on at least one side of the footplate.

The extension to the width of the footplate preferably increases the width of the footplate by at least 0.25 cm at its widest point, more preferably by at least 0.5 cm or 1.0 cm at its widest point, and most preferably by at least 1.5 cm at its widest point.

The extension to the width of the footplate preferably increases the width of the footplate by between 0.25 cm and 10.0 cm at its widest point, more preferably by between 0.5 cm and 7.5 cm or between 1.0 cm and 5.0 cm at its widest point, and most preferably by between 1.5 cm and 2.5 cm at its widest point.

In a preferred embodiment, the second portion defines an extension to both sides of the footplate.

Accordingly, the extension to the width of the footplate preferably increases the width of the footplate by at least 0.125 cm on each side at its widest point, more preferably by at least 0.25 cm or 0.5 cm on each side at its widest point, and most preferably by at least 0.75 cm on each side at its widest point.

The extension to the width of the footplate preferably increases the width of the footplate by between 0.125 cm and 5.0 cm on each side at its widest point, more preferably by between 0.25 cm and 3.75 cm or between 0.5 cm and 2.5 cm on each side at its widest point, and most preferably by between 0.75 cm and 1.25 cm on each side at its widest point.

Preferably, the second portion extends around the peripheral edge of the orthosis at least adjacent to the position of the subject's toes when the orthosis is worn by a subject.

In a preferred embodiment, an area adjacent to the front of the footplate and an area adjacent to a portion of both sides and toward the front of the footplate comprises the second portion.

Advantageously, this allows the front and sides of the footplate to be trimmed such that the orthosis may be configured to fit a range of different shoe sizes. Additionally, the low Young's modulus of the second portion is advantageous due to the large flexural range of movement that occurs in this area during walking.

Preferably, an area at least adjacent and/or towards the back of the footplate comprises the first portion. Preferably, the strut comprises the first portion. Preferably, the calf abutment member comprises the first portion.

Preferably, in embodiments where the plurality of first fibres comprise unidirectional fibres, the unidirectional fibres are disposed in the footplate and aligned substantially parallel to the long axis of the foot of a subject. It may be understood that the long axis of the foot is a theoretical straight line between the middle of the heel through the second toe of the subject.

Advantageously, the unidirectional fibres strengthen the footplate along the long axis.

In a preferred embodiment the strut, the calf abutment member and the area adjacent to the back of the footplate comprise the first portion.

Advantageously, the majority of the orthosis is defined by the first portion. Accordingly, it will have a high tensile strength.

In accordance with a second aspect, there is provided a method of making an orthosis comprising:
  providing a tool corresponding to a subject's body part;
  positioning a first curable material comprising a plurality of first fibres over a first portion of the tool;
  positioning a second curable material comprising a plurality of second fibres over a second portion of the tool; and
  curing the first and second curable materials so that they form an orthosis comprising a first portion comprising a polymer reinforced with the plurality of first fibres and a second portion comprising a polymer reinforced with a plurality of second fibres;
characterised in that the first portion has a higher tensile strength and is harder than the second portion.

Preferably, the method of the second aspect is used to manufacture an orthosis according to the first aspect.

The first and second curable materials may be either a UV-curable or a heat-curable material. Preferably, the first and second curable materials are in sheet form. In some embodiments, the first and second curable materials may be tensioned after they have been applied to the polymeric material. In other embodiments, tensioning is not required.

Preferably, the first curable material comprises at least one composite sheet including an inner core of the plurality of first fibres impregnated with a polymer resin. Preferably, the second curable material comprises at least one composite sheet including an inner core of the plurality of second fibres impregnated with a polymer resin. In a preferred embodiment, the first curable material comprises at least one composite sheet including an inner core of the plurality of first fibres impregnated with a polymer resin and the second curable material is at least one composite sheet including an inner core of the plurality of second fibres impregnated with a polymer resin.

The or each composite sheet may be of the type often referred to as a "pre-preg", in that it comprises a fibre composite sheet pre-impregnated with resin.

The first and second curable materials are preferably uncured at the time of being placed over the tool. Advantageously, this allows the curable material to be carefully worked around the 3D shape of the tool. Preferably, the plurality of first and second fibres are manipulated, such that they form a three dimensional shape represented by the tool. Due to the tacky uncured resin, the pre-preg holds its position well on the tool surface.

Preferably, the first fibres comprise carbon fibres. More preferably, the first fibres consist of carbon fibres. Accordingly, the only fibres in the first portion are preferably carbon fibres.

The inner core of the plurality of first fibres may comprise unwoven fibres. The unwoven fibres may comprise unidirectional fibres. Additionally, or alternatively, the inner core of the plurality of first fibres may comprise woven fibres. The woven fibres may comprise twill fibres.

In a preferred embodiment, the first curable material is a plurality of composite sheets, each sheet including an inner core of the plurality of first fibres impregnated with a polymer resin. Preferably, the plurality of composite sheets comprise at least one sheet wherein the inner core of the plurality of first fibres comprises unwoven fibres and at least one sheet wherein the inner core of the plurality of first fibres comprises woven fibres. More preferably, the plurality of composite sheets comprise at least one sheet wherein the inner core of the plurality of first fibres comprises unwoven fibres sandwiched between two sheets wherein the inner core of the plurality of first fibres comprises woven fibres.

Accordingly, positioning a first curable material comprising a plurality of first fibres over a first portion of the tool may comprise:
  positioning a composite sheet including a woven inner core of the plurality of first fibres impregnated with a polymer resin over the first portion of the tool;
  positioning at least one composite sheet including an unwoven inner core of the plurality of first fibres impregnated with a polymer resin over the first portion of the tool; and
  positioning a further composite sheet including a woven inner core of the plurality of first fibres impregnated with a polymer resin over the first portion of the tool.

In a preferred embodiment, the tool corresponds to at least a portion of a leg. Preferably, the first portion of the tool corresponds to at least a portion of the sole of a foot. Preferably, the unwoven inner core of the at least one composite sheet including an unwoven inner core of the plurality of first fibres comprises unidirectional fibres and the unidirectional fibres are substantially aligned with the elongate axis of the foot.

Preferably, the second fibres comprise glass fibres. More preferably, the second fibres consist of glass fibres. Accordingly, the only fibres in the second portion are preferably glass fibres.

The inner core of the plurality of second fibres may comprise unwoven fibres. The unwoven fibres may comprise unidirectional fibres. Additionally, or alternatively, the inner core of the plurality of second fibres may comprise woven fibres. The woven fibres may comprise twill fibres.

In a preferred embodiment the inner core of the plurality of second fibres comprise twill glass fibres.

In a preferred embodiment, the second curable material comprises a plurality of composite sheets, each sheet including an inner core of the plurality of second fibres impregnated with a polymer resin. In a more preferred embodiment, the second curable material comprises a plurality of composite sheets, each sheet including an inner core of woven glass fibres impregnated with a polymer resin.

Preferably, the method comprises positioning the first curable material and the second curable material over a third portion of the tool disposed between the first and second portions.

Accordingly, in one preferred embodiment, the method comprises:
providing a tool corresponding to a subject's body part;
positioning a first curable material comprising a plurality of first fibres over the first portion and the third portion of the tool;
positioning a second curable material comprising a plurality of second fibres over the second portion and the third portion of the tool; and
curing the first and second curable materials.

In a more preferred embodiment, the method comprises:
a) providing a tool corresponding to a subject's body part;
b) positioning a composite sheet including an inner core of the plurality of second fibres impregnated with a polymer resin over the second portion and the third portion of the tool;
c) positioning a composite sheet including an inner core of the plurality of first fibres impregnated with a polymer resin over the first portion and the third portion of the tool;
d) positioning a further composite sheet including an inner core of the plurality of second fibres impregnated with a polymer resin over the second portion and the third portion of the tool; and
e) curing the first and second curable materials.

Accordingly, the third portion preferably comprises a plurality of first fibres sandwiched between a plurality of second fibres.

In a most preferred embodiment, the method comprises:
a) providing a tool covered with a polymeric material, wherein the tool corresponds to a subject's body part;
b) positioning a composite sheet including a woven inner core of the plurality of second fibres impregnated with a polymer resin over a second portion and a third portion of the tool;
c) positioning a composite sheet including a woven inner core of the plurality of first fibres impregnated with a polymer resin over a first portion and the third portion of the tool;
d) positioning at least one composite sheet including an unwoven inner core of the plurality of first fibres impregnated with a polymer resin over the first portion and the third portion of the tool;
e) positioning a further composite sheet including a woven inner core of the plurality of first fibres impregnated with a polymer resin over a first portion and the third portion of the tool;
f) positioning a further composite sheet including a woven inner core of the plurality of second fibres impregnated with a polymer resin over the second portion and the third portion of the tool; and
g) curing the first and second curable materials.

Preferably, the method comprises providing a dye and/or pigment in the second portion which affects the colour of the second portion. The method preferably comprises providing the dye and/or pigment in the second curable material, and most preferably in the resin of the second curable material. Preferably, the pigment and/or dye is selected to ensure that the second portion is visually distinct from the first portion.

The method preferably comprises disposing a layer of polymeric material over the tool prior to positioning the first and second curable materials over the tool. Subsequent to positioning the first and second curable materials over the tool, and prior to curing the first and second curable materials, the method may comprise wrapping a releasable membrane over the tool and the first and second curable materials. The membrane may be a polytetrafluoroethylene-based film. A vacuum-permeable breather fabric may be placed over the releasable membrane. This resultant structure may then be placed in a heat-tolerant vacuum bag comprising a vacuum valve.

The vacuum bag-enclosed tool may be placed in an oven (e.g. convection oven) or an autoclave. The oven or autoclave may have a vacuum tube entering into it through an aperture in one side thereof. The tool is preferably placed under vacuum pressure whilst in the oven or autoclave.

Advantageously, the vacuum pressurises the first and second curable materials thereby sucking out any air trapped within the substrate consisting of the tool and curable materials. Any resultant air bubbles would act to weaken the structure.

The temperature in the oven or autoclave may be gradually increased until it reaches a curing temperature. The temperature may be increased over at least 10 minutes, more preferably, at least 20 minute or 30 minutes, and most preferably at least 40 minutes.

The tool may then be heated for at least 1 hour or 2 hours at the curing temperature.

Preferably, the tool is heated for between 1 hour and 5 hours at a curing temperature. More preferably, the tool is heated for between 2 hours and 4 hours at a curing temperature. Most preferably, the tool is heated for about 3 hours at a curing temperature.

The curing temperature is preferably between 60° C. and 180° C., more preferably between 70° C. and 170° C., between 80° C. and 160° C. or between 90° C. and 150° C., and most preferably between 100° C. and 140° C., or between 110° C. and 130° C.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which.

EXAMPLES

Figure 1:
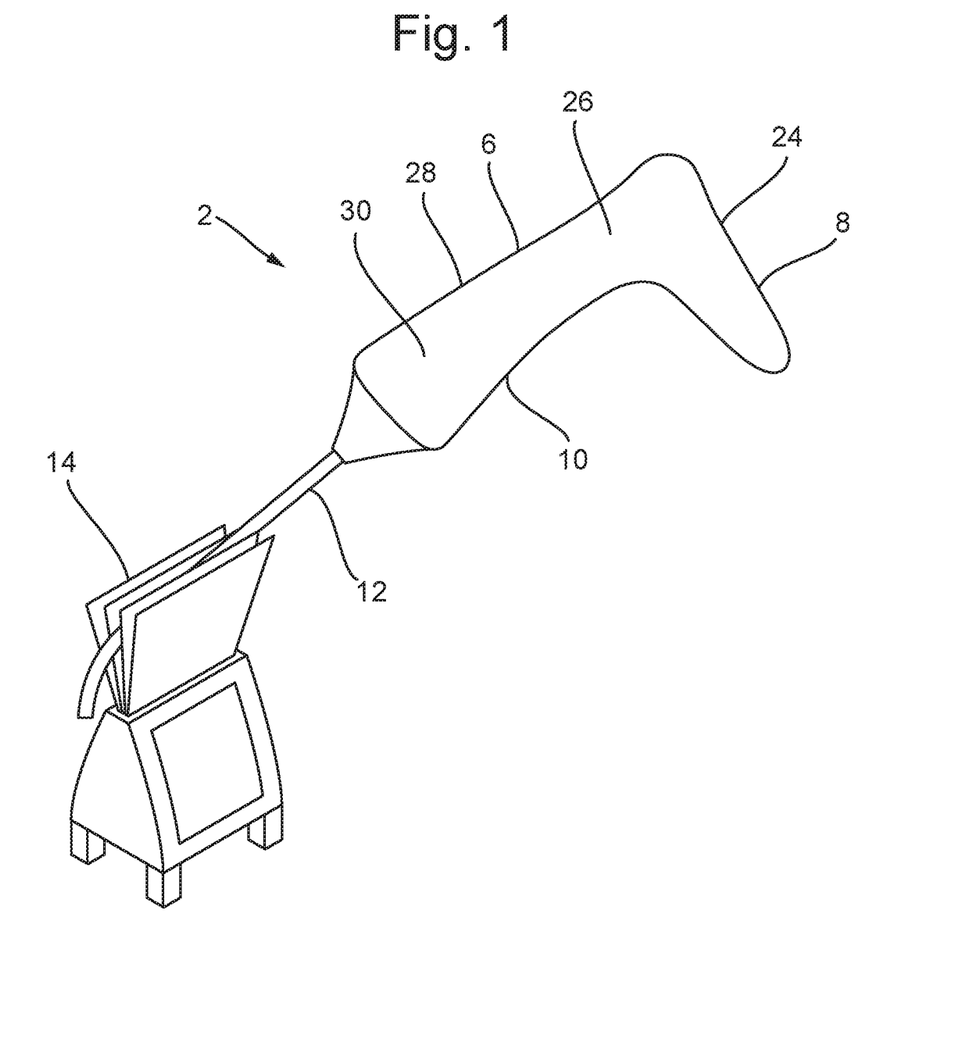
FIG. 1 is a perspective view of a plaster cast of a patient's leg forming a tool that is used for preparing an orthotic device according to the invention.
Figure 4:
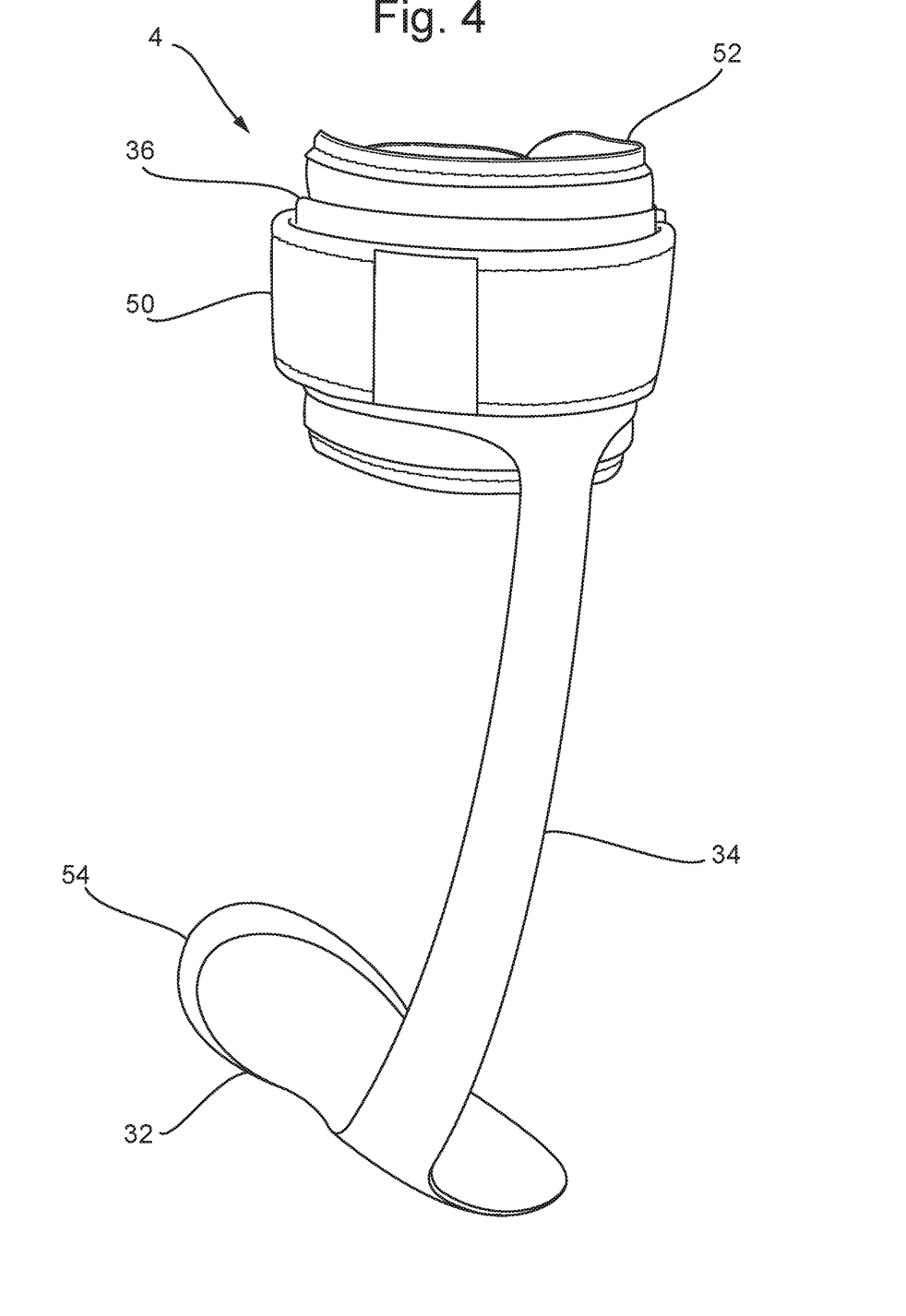
FIG. 4 is a perspective rear view of an ankle foot orthotic (AFO) made using an embodiment of the method of the present invention.
Figure 5:
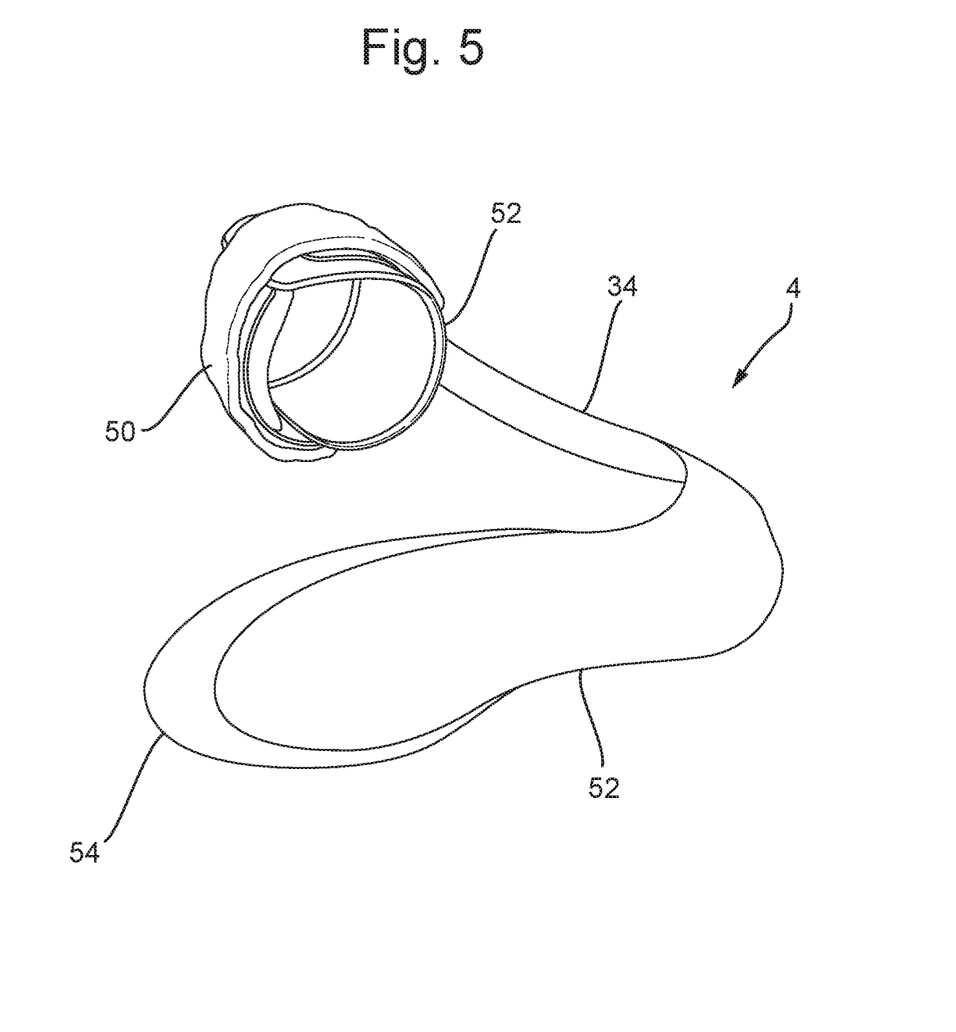
FIG. 5 is a perspective view from underneath the AFO shown in FIG. 4.
Figure 6:
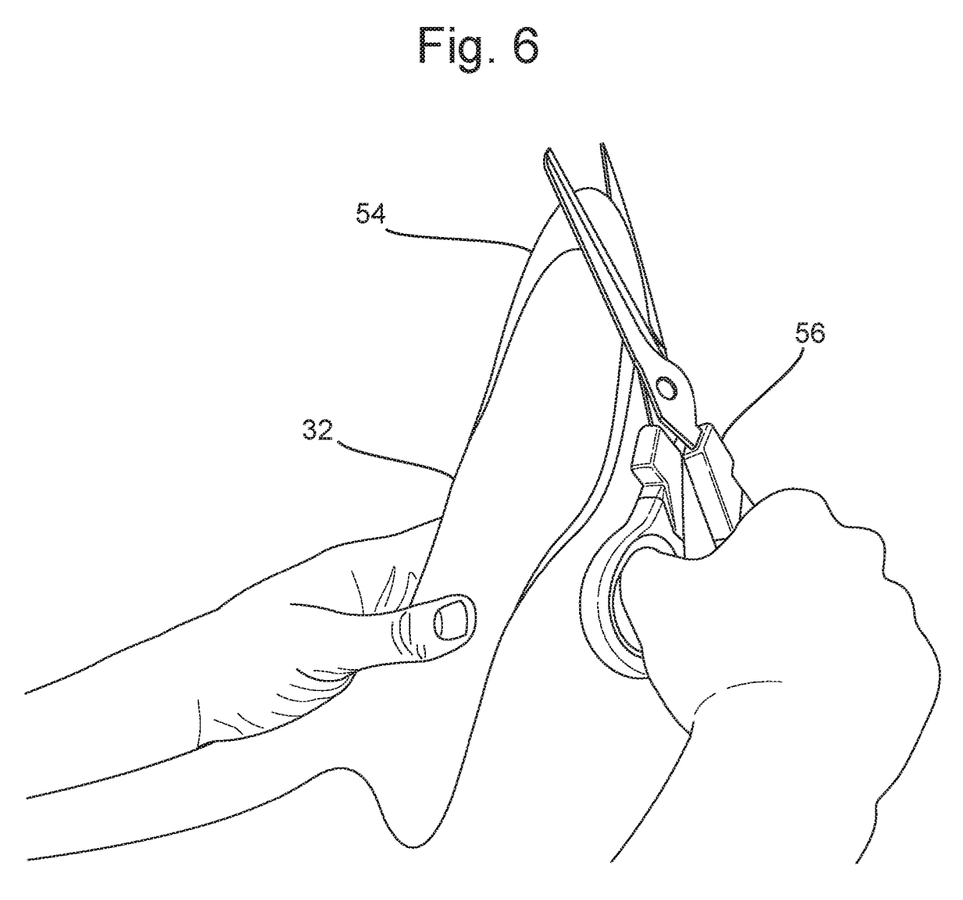
FIG. 6 is a perspective view of the AFO shown in FIGS. 4 and 5 being trimmed using scissors.

Plaster of Paris is safe, adaptable and cheap. Accordingly, Plaster of Paris is used in orthotic and prosthetic manufacturing to both capture the shape of a person's anatomy and modify a workable and unique 'tool' 2 for manufacturing. An example of a tool 2 used to make an orthosis 4 shown in FIGS. 4-6 is shown in FIG. 1. A unique tool 2 may be made for each individual who requires the orthosis 4.

Alternatively, it is possible to use a standard tool 2 to create multiple identical orthoses 4, which reduces costs but means that it may be necessary for the size and fitting of the orthoses 4 to be adjusted after manufacture to ensure they are suitable for the user. A standard tool is usually made using a pourable two part epoxy 'tooling' resin, or milled from a pre-fabricated block of 'epoxy tooling board'. These materials are more durable than plaster allowing use for multiple cures, for instance the inventors aim for over 1000 cures per tool.

The tool 2 comprises a plaster portion 6 corresponding in shape to a portion of the client's anatomy, for example an arm, leg or foot. In the embodiment illustrated in FIG. 1, the tool corresponds to a person's foot 8 and lower leg 10. A metal rod 12 extends out from the plaster portion 6, by which the tool 2 can be held steady by locating the metal rod 12 in a clamp 8. The rod 12 is hollow and also provides the source of vacuum pressure, as described below.

Figure 2:
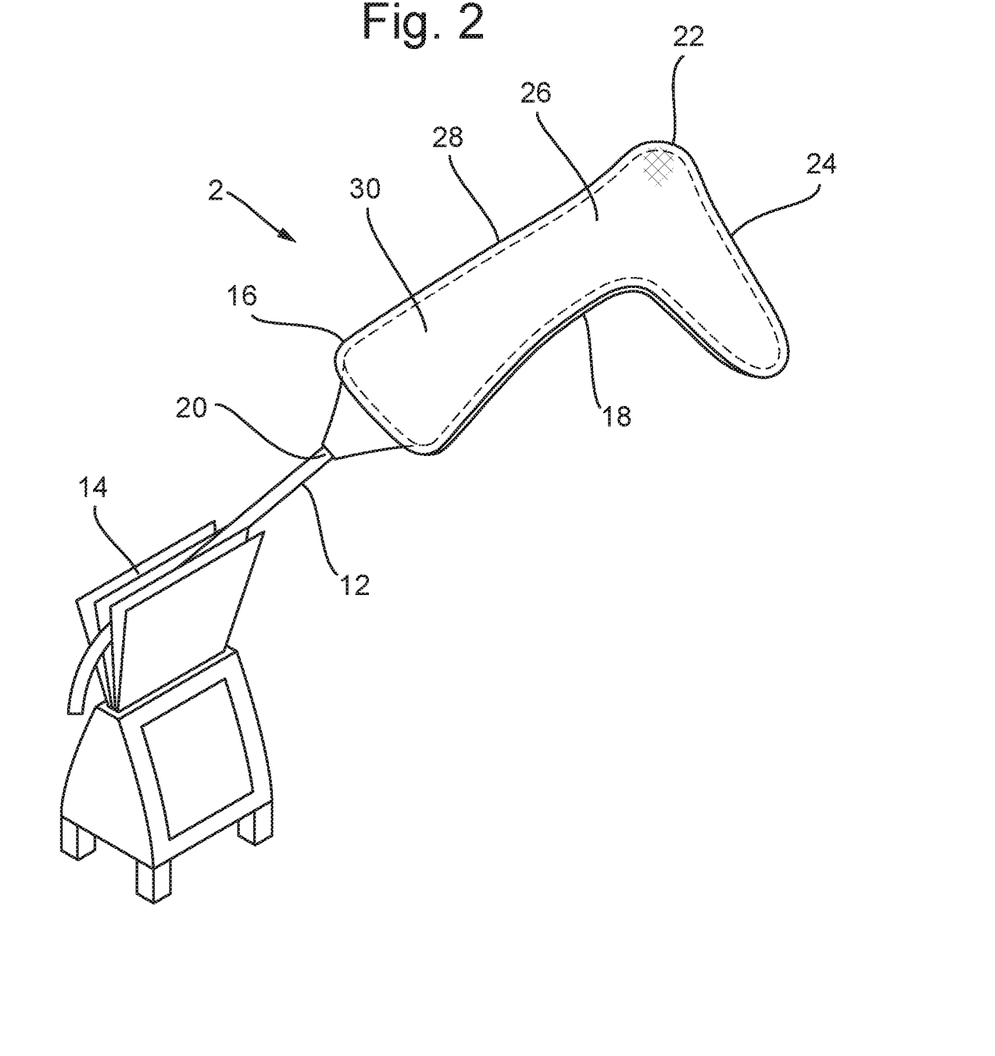
FIG. 2 is a perspective view of the plaster cast of a patient's leg of FIG. 1 with a polymeric sheet fitted thereto.

A 1 to 2 mm thick layer of homopolymer polypropylene sheet 16 is heated in an infrared oven at 190° C. for 30 minutes. When warm, the polypropylene sheet 16 is then draped over the plaster portion 6 of the tool 2 and a seal 18 is created by joining the partially molten sheet 16 around the tool 2 with light pressure applied from the technician's glove-protected hands to join it to itself, as shown in FIG. 2. A further seal 20 is also created around the rod 12.

As mentioned above, the hollow rod 12 is inserted into the plaster portion 6. This allows ease of handling, and also allows the rod 12 to be connected to a vacuum system (not shown). For example, the rod 12 can be connected to a rotary vane vacuum pump or a domestic vacuum cleaner. One hole in the rod 12 is usually sufficient to create sufficient vacuum pressure to seal the polypropylene around the tool 2. However, on larger tools 2, it may be preferred to drill into the internal rod 12 in suitable sections in order to spread the vacuum pressure sufficiently. The vacuum is maintained until the polypropylene has cooled, which is usually at ambient temperature or about 21° C. The length of time for allowing cooling depends upon the ambient room temperature. For example, if the polypropylene is maintained at about 21° C., it can take about 45 minutes to cool sufficiently.

After the polypropylene 16 has cooled, the vacuum is removed and the polypropylene sheet 16 retains the shape of the tool 2. The polypropylene-covered tool 2 can then be moved freely around the workshop using rod 12, as it is no longer tied to the vacuum system.

As shown in FIG. 2, pre-impregnated (pre-preg) fibres 22 are then placed on the polypropylene-covered tool 2 in the desired locations for making the orthosis. To make the orthosis 4 shown in FIGS. 4 to 6, the fibres 22 are placed on the sole 24 of the foot 8, and laid to define a strut which runs along the side 26, and around the back 28 of the leg 10 and then extends around a portion of the calf 30.

To make the orthosis 4 shown in FIGS. 4 to 6, three different types of pre-impregnated fibres are used: (i) carbon twill fibres having a weight of 200 gsm (grams per square meter); (ii) carbon unidirectional fibres having a weight of 300 gsm; and (iii) glass twill fibres having a weight of 200 gsm.

All of the fibres were pre-impregnated with epoxy resins configured to be cured at a medium temperature, i.e. about 120° C. Both sets of carbon fibres impregnated with resin (i.e. (i) and (ii) mentioned above) have a higher tensile strength, and are harder, than the glass fibres in resin (i.e. (iii) mentioned above). Accordingly, the glass fibre in resin composite can be readily cut or trimmed using scissors, or the like, as discussed in detail below.

It will be appreciated that carbon fibres (i) and (ii) are substantially opaque, or black, whereas the glass fibres are substantially translucent or transparent. The inventors have used pre-impregnated glass fibres which are impregnated with a pigment, for example a blue pigment, which clearly demarks where the carbon fibres end and the glass fibres begin, as discussed below. In particular, the inventors have used a generic royal blue epoxy pigment that is widely available. The inventors found that a weight ratio of about 1 wt % pigment to 99 wt % epoxy resin achieves a visually distinct colour while maintaining some translucency in the final composite structure. However, it will be appreciated that this weight ratio may be varied for different pigments.

With reference to FIGS. 3*a-f*, the various pre-impregnated fibres 22 need to be cut to a specific shape and placed on the tool 2 in a specific order. By way of example, this process is explained by reference to the fibres which were placed on the sole 24 of the foot 8, to create a footplate 32. However, it will be appreciated that a similar process will also be used to define the strut 34 and cuff 36 of the orthosis 4.

Firstly, two layers of glass twill fibres 41 are placed on the sole 24 of the foot 8. However, it is not necessary for the glass fibres 41 to extend to the back of the footplate, as these fibres 41 only have to be disposed in areas where the orthosis 4 may need to be cut, which is generally at and towards the front of the footplate 32, and around the peripheral edge thereof, as shown in FIG. 5.

Figure 3A:
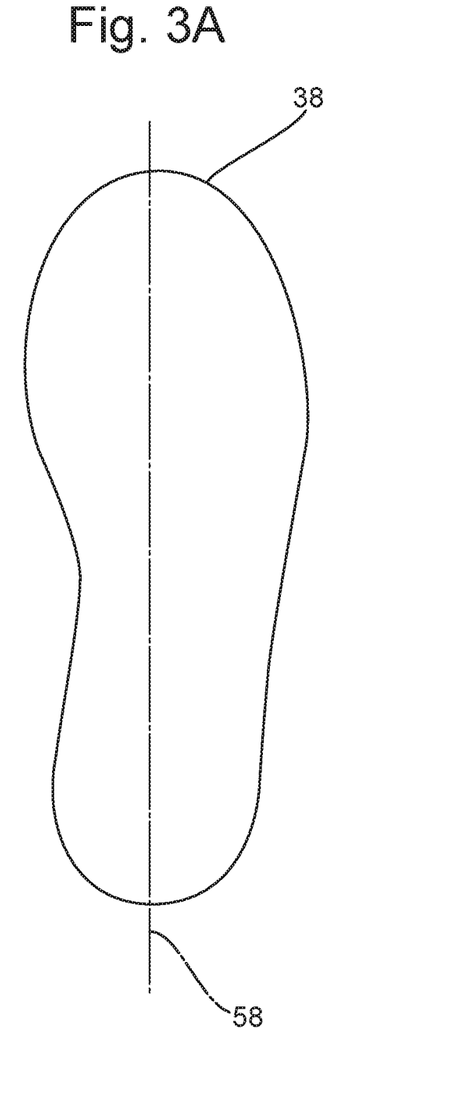
FIGS. 3A-F are plan views showing various templates which determine how pre-impregnated fibres should be laid on the sole of the foot of the tool of FIGS. 1 and 2.
Figure 3B:
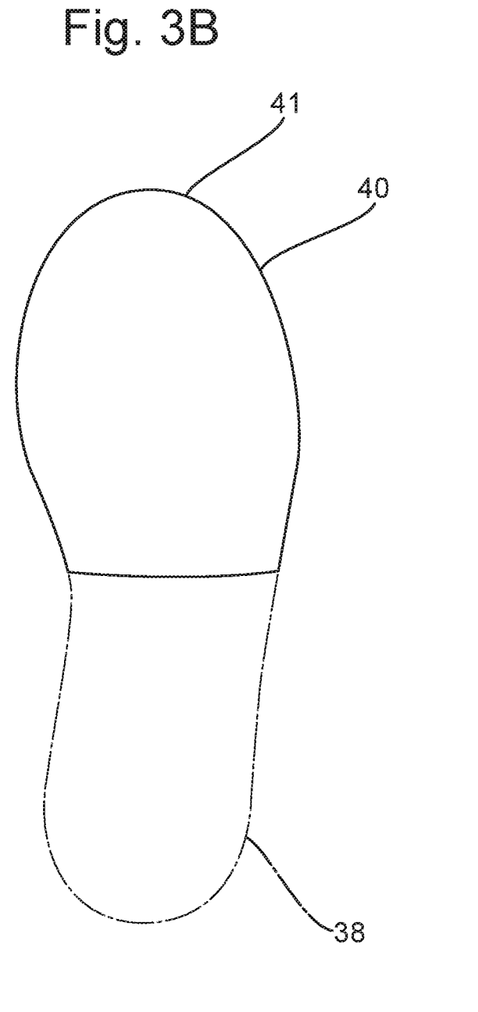

FIG. 3*a* shows the full footplate template 38, i.e. this is the total area of the footplate 32 in the completed orthosis 4. By comparison, FIG. 3*b* shows a forefoot template 40 which shows where the layers of glass twill fibres 41 are positioned on the sole 24 of the foot 8. For comparison, the full footplate template 38 is shown as a dotted line in FIG. 3*b*.

Next, a layer of carbon twill fibres 43 are placed on the sole 24 of the foot 8. However, these fibres 43 are not desirable in locations where the orthosis 4 may need to be cut. Accordingly, the layer of carbon twill fibres 43 corresponds to the short footplate template 42 shown in FIG. 3*c*.

Next, four layers of carbon unidirectional fibres 45, 47, 49, 51 are placed on the sole 24 of the foot 8. The first layer 45 corresponds to the short footplate template 42, the second layer 47 corresponds to the first backfoot template 44, shown in FIG. 3*d*, the third layer 49 corresponds to the second backfoot template 46, shown in FIG. 3*e*, and the fourth layer 51 corresponds to third backfoot template 48, shown in FIG. 3*f*.

The layers of unidirectional carbon fibres 45, 47, 49, 51 are positioned to ensure that the fibres align along the long axis of foot 58 when the orthosis is being worn by a subject. The long axis of the foot 58 is a theoretical straight line between the middle of the heel through the second toe, and is shown in FIG. 3*a*. The footplate is subjected to a variety of forces along the long axis 58 as a user walks, and the unidirectional carbon fibres 45, 47, 49, 51 increase the strength of the footplate along this axis.

Figure 3C:
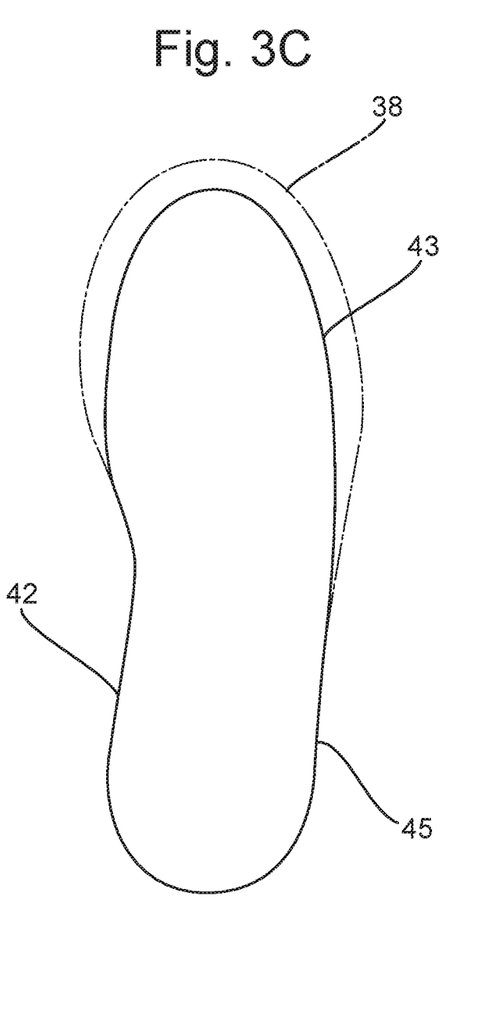
Figure 3D:
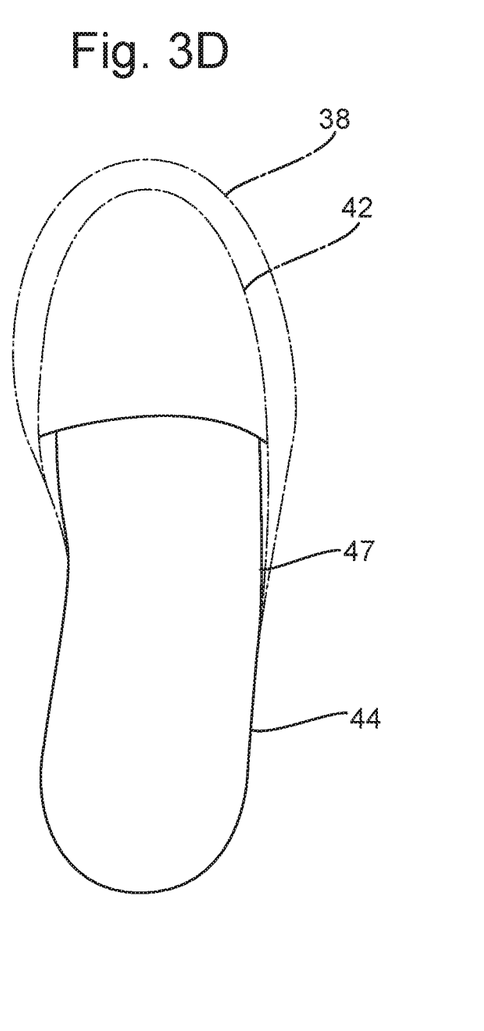
Figure 3E:
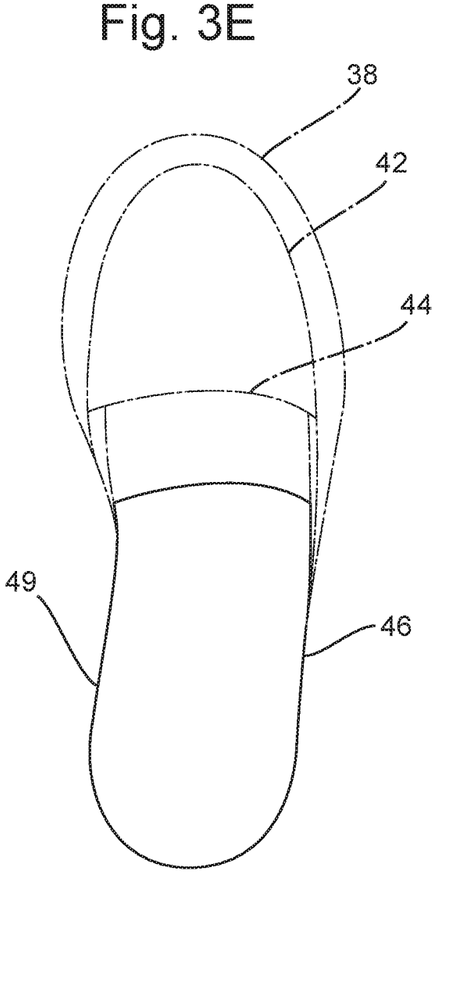
Figure 3F:
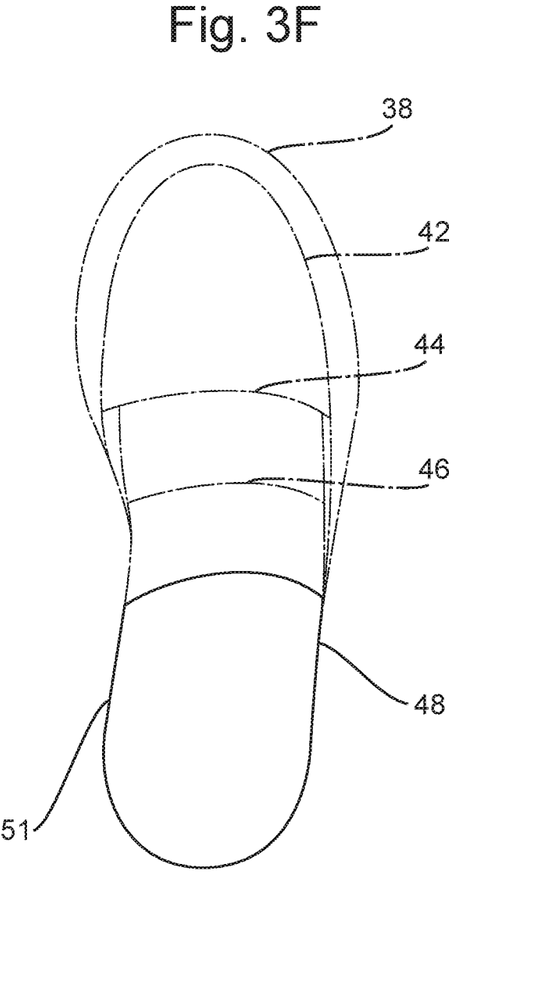

A further layer of carbon twill fibres 43 corresponding to the short footplate template 42, followed by a final two layers of glass fibres 41 corresponding to the forefoot template 40 are then placed on the sole 24 of the foot 8.

The twill fibres 43 cross the unidirectional fibres 45, 47, 49, 51 and offer a transverse strength. Accordingly, the twill fibres 43 'ties in' and supports the unidirectional fibres 45, 47, 49, 51. This ensures that the resulting orthosis has a strong footplate 32 along the long axis of the foot 58 with some flexibility when twisted. Accordingly, if a user steps on a pebble on the outside of their foot the structure moves to accommodate it rather than being too rigid.

It will be appreciated that when these fibres 22 are placed on the tool 2, manipulation of the fibre weave over and around polymeric material on the tool 2 may be required. Thus, the fibres 22 are manipulated such that they form a three dimensional shape represented by the tool. Due to the tacky uncured resin, the pre-preg holds the position well on the tool 2 surface.

The carbon fibres 22 are then cured. The step of curing the fibres can involve either UV-curing or heat-curing the curable material. The pre-preg is wrapped in a releasable membrane, such as a polytetrafluoroethylene-based film. A vacuum-permeable breather fabric is then placed over the releasable membrane, and this resultant structure is then placed in a heat-tolerant vacuum bag comprising a vacuum valve. The vacuum bag-enclosed tool is then placed in a convection oven (or an autoclave). The oven or autoclave has a vacuum tube entering into it through an aperture in one side thereof. The tool 2 is placed under vacuum pressure whilst in the oven or autoclave. The vacuum pressurises the pre-preg thereby sucking out any air trapped within the substrate. Any resultant air bubbles would only act to weaken the structure. The temperature in the oven or autoclave is increased over 45 minutes until it reaches 120° C. The tool 2 is then maintained at 120° C. for 3 hours.

The resultant orthosis 4 is removed 'demoulded' from the tool 2 by mechanically prying it off the tool 2. The polypropylene sheet 16 does not stick to the resin, and so this process is straightforward unless there is some sort of geometry that 'locks' the device in place. The orthoses usually requires their edges to be smoothed. Then straps 50 and padding 52 can be added to the orthosis 4.

As shown in FIGS. 4 to 6, the use of pre-impregnated glass fibres 41 provided with a blue pigment results in the trimmable area 54 being easily identifiable. This can be trimmed using scissors 56 to enable the orthosis 4 to better fit a user.

The act of cutting trimmable area 54 with scissors 56 requires the pre-impregnated glass fibres 41 to fracture as the scissors 56 exert a force upon them. Carbon fibres outperform glass fibres in tensile, compressive, flexural and bend strength. As such when scissors 56 are applied to the trimmable area 54 it is possible to fracture the pre-impregnated glass fibres 41, and thereby cut through the composite material. However, it is not possible to fracture a carbon fibre composite using scissors 56. Accordingly, it will not be possible to cut the remainder of the orthosis 4.

The invention claimed is:

1. An orthosis comprising a first portion which comprises a polymer reinforced with a plurality of first fibres, and a trimmable second portion which is disposed around at least a section of a peripheral edge of the orthosis and comprises a polymer reinforced with a plurality of second fibres, wherein the first portion has a higher tensile strength and is harder than the second portion, and wherein the second portion comprises a pigment and/or a dye which affects the colour of the second portion, wherein the pigment and/or dye is selected to ensure that the second portion is visually distinct from the first portion, so that in use the trimmable area of the second portion is easily identified and can be trimmed to enable the orthosis to better fit a user.

2. An orthosis according to claim 1, wherein the orthosis comprises a lower limb orthosis, and the lower limb orthosis is selected from the group consisting of a foot orthosis, an ankle-foot orthosis (AFO), a knee-ankle-foot orthosis (KAFO), a knee orthosis and a hip-knee-ankle-foot orthosis (HKAFO), and the orthosis comprises a footplate configured to extend beneath the sole of a foot of a subject, and the footplate comprises a front which is configured to extend beneath the toes of the subject, a back which is configured to extend beneath a heel of the subject, and two sides which are configured to extend between the front and the back.

3. An orthosis according to claim 2, wherein an area at least adjacent and/or towards the front of the footplate comprises the second portion, thereby defining an extension to a length of the footplate.

4. An orthosis according to claim 3, wherein the extension to the length of the footplate increases the length of the footplate by at least 0.5 cm, 1.0 cm, 1.5 cm, 2.0 cm or 2.5 cm at its longest point.

5. An orthosis according to claim 2, wherein the orthosis comprises an ankle-foot orthosis (AFO).

6. An orthosis according to claim 2, wherein an area at least adjacent and/or towards a region of one or both sides of the footplate comprises the second portion, thereby defining an extension to a width on at least one side of the footplate.

7. An orthosis according to claim 6, wherein the area at least adjacent and/or towards a region of one or both sides of the footplate is also at least adjacent and/or towards the front of the footplate.

8. An orthosis according to claim 6, wherein the extension to the width of the footplate increases the width of the footplate by at least 0.25 cm, 0.5 cm, 1.0 cm or 1.5 cm at its widest point.

9. An orthosis according to claim 2, wherein an area at least adjacent and/or towards the back of the footplate comprises the first portion.

10. An orthosis according to claim 9, wherein the plurality of first fibres comprise unidirectional fibres, and the unidirectional fibres are disposed in the footplate and configured to be aligned substantially parallel to a long axis of the foot of a subject.

11. An orthosis according to claim 1, wherein the first fibres comprise carbon fibres.

12. An orthosis according to claim 11, wherein the only fibres in the first portion are carbon fibres.

13. An orthosis according to claim 1, wherein the second fibres comprise glass fibres.

14. An orthosis according to claim 13, wherein the only fibres in the second portion are glass fibres.

15. An orthosis according to claim 1, wherein the orthosis comprises a third portion disposed between the first and second portions, and comprising a polymer reinforced with a plurality of first and second fibres.

16. An orthosis according to claim 1, wherein the polymer of the first and second portions comprise a thermoplastic material or a thermosetting material.

17. An orthosis according to claim 1, wherein the second portion is substantially translucent or transparent.

18. A method of making an orthosis comprising:
   providing a tool corresponding to a subject's body part;
   positioning a first curable material comprising a plurality of first fibres over a first portion of the tool;
   positioning a second curable material comprising a plurality of second fibres over a second portion of the tool; and
   curing the first and second curable materials so that they form an orthosis comprising a first portion comprising a polymer reinforced with the plurality of first fibres and a second portion comprising a polymer reinforced with a plurality of second fibres;

characterised in that the first portion has a higher tensile strength and is harder than the second portion and the pigment and/or a dye affects the colour of the second portion, wherein the pigment and/or dye is selected to ensure that the second portion is visually distinct from the first portion, so that in use the trimmable area of the second portion is easily identified and can be trimmed to enable the orthosis to better fit a user.

19. A method according to claim 18, wherein the method comprises:

a) providing a tool covered with a polymeric material, wherein the tool corresponds to a subject's body part;

b) positioning a composite sheet including a woven inner core of the plurality of second fibres impregnated with a polymer resin over a second portion and a third portion of the tool;

c) positioning a composite sheet including a woven inner core of the plurality of first fibres impregnated with a polymer resin over a first portion and the third portion of the tool;

d) positioning at least one composite sheet including an unwoven inner core of the plurality of first fibres impregnated with a polymer resin over the first portion and the third portion of the tool;

e) positioning a further composite sheet including a woven inner core of the plurality of first fibres impregnated with a polymer resin over a first portion and the third portion of the tool;

f) positioning a further composite sheet including a woven inner core of the plurality of second fibres impregnated with a polymer resin over the second portion and the third portion of the tool; and g) curing the first and second curable materials.

* * * * *